United States Patent [19]

Nohe et al.

[11] 4,086,250

[45] Apr. 25, 1978

[54] MANUFACTURE OF BICYCLO[2,2,2]OCT-7-ENE 2,3,5,6-TETRACARBOXYLIC ACID DIANHYDRIDE

[75] Inventors: Heinz Nohe, Meckenheim; Heinz Hannebaum, Ludwigshafen, both of Germany

[73] Assignee: BASF Aktiengesellschaft, Ludwigshafen, Germany

[21] Appl. No.: 743,516

[22] Filed: Nov. 19, 1976

[30] Foreign Application Priority Data

Dec. 9, 1975 Germany .............................. 2555254

[51] Int. Cl.² .......................................... C07D 307/93
[52] U.S. Cl. .................................................. 260/346.6
[58] Field of Search ..................................... 260/346.6

[56] References Cited

U.S. PATENT DOCUMENTS

| 3,125,585 | 3/1964 | Yates .............................. 260/346.6 X |
| 3,522,277 | 7/1970 | Suter et al. ......................... 260/346.6 |

FOREIGN PATENT DOCUMENTS 1,228,623  4/1971  United Kingdom .............. 260/346.6

OTHER PUBLICATIONS

Cassidy, Technique of Organic Chemistry, vol. 5, (Adsorption and Chromatography), Interscience Publishers, Inc., New York, (1951), pp. 188 to 198.

*Primary Examiner*—Richard L. Raymond
*Attorney, Agent, or Firm*—Keil, Thompson & Shurtleff

[57] ABSTRACT

Bicyclo[2,2,2]oct-7-ene-2,3,5,6-tetracarboxylic acid dianhydride is manufactured by reacting 3,5-cyclohexadiene-1,2-trans-dicarboxylic acid with maleic acid in the presence of anhydrides of low molecular weight alkanecarboxylic acids at from 50° to 150° C. The 3,5-cyclohexadiene-1,2-trans-dicarboxylic acid, in the anhydride of the low molecular weight alkanecarboxylic acid, and in the presence of water-soluble salts of the alkali metals, of the alkaline earth metals or of zinc, manganese or iron, in which salts the anion contains oxygen, is first heated to the reaction temperature and the maleic anhydride is then added.

7 Claims, No Drawings

MANUFACTURE OF BICYCLO[2,2,2]OCT-7-ENE 2,3,5,6-TETRACARBOXYLIC ACID DIANHYDRIDE

The present invention relates to a new process for the manufacture of bicyclo[2,2,2]oct-7-ene-2,3,5,6-tetracarboxylic acid dianhydride.

German Published Application 1,234,211 discloses that 3,6-endoethyleno-1,2,4,5-cyclohexanetetracarboxylic acid dianhydride (= bicyclo[2,2,2]oct-7-ene-2,3,5,6-tetracarboxylic acid dianhydride, "BTA") can be manufactured by reacting 3,5-cyclohexadiene-1,2-dicarboxylic acid with maleic anhydride in the presence of acetic anhydride at from 50° to 150° C. This process gives good results if the cyclohexadienedicarboxylic acid is extremely pure. If, for example, cyclohexadienedicarboxylic acid which has been manufactured by electrochemical reduction of o-phthalic acid is used, it requires careful and expensive purification, for example by recrystallization from boiling water in the presence of active charcoal. The troublesome impurities are not detectable analytically and only manifest themselves by reducing the yield of the reaction with maleic anhydride.

German Patent No. 1,643,654 discloses that bicyclo[2,2,2]oct-7-ene-2,3,5,6-tetracarboxylic acid dianhydride can advantageously be manufactured by reacting 3,5-cyclohexadiene-1,2-dicarboxylic acid with maleic anhydride in the presence of anhydrides of low molecular weight alkanecarboxylic acids at from 50° to 150° C, if the 3,5-cyclohexadiene-1,2-dicarboxylic acid, in the anhydride of the low molecular weight alkanecarboxylic acid and in the presence of adsorbents, such as active charcoal having an inner surface area of 500 m$^2$/g, fuller's earths, silica gel, aluminum oxides or aluminum hydroxides, is first heated to the reaction temperature, and the maleic anhydride is only then added.

An example of the disadvantages of this process is that both the metering of the adsorbent and the handling of the suspension present difficulties and the yield is reduced by separating off the adsorbent.

We have found that the above disadvantages can be avoided in the manufacture of bicyclo[2,2,2]oct-7-ene-2,3,5,6-tetracarboxylic acid dianhydride by reacting 3,5-cyclohexadiene-1,2-trans-dicarboxylic acid with maleic anhydride in the presence of anhydrides of low weight alkanecarboxylic acids at from 50° to 150° C, in which the 3,5-cyclohexadiene-1,2-trans-dicarboxylic acid in the anhydride of the low molecular weight alkanecarboxylic acid is first heated to the reaction temperature and the maleic anhydride is then added, if the heating of the 3,5-cyclohexadiene-1,2-trans-dicarboxylic acid in the anhydride of the low molecular weight alkanecarboxylic acid is carried out in the presence of water-soluble salts of the alkali metals, of the alkaline earth metals or of zinc, manganese or iron, in which salts the anion contains oxygen.

Examples of water-soluble salts of the alkali metals, of the alkaline earth metals or of zinc, manganese or iron, which contain oxygen in the anion, are the oxides, hydroxides, carbonates, acetates, oxalates or nitrates of the alkali metals and the acetates of the alkaline earth metals or of zinc, manganese or iron. Specific examples which may be mentioned are sodium acetate, potassium acetate, lithium hydroxide, iron acetate, calcium acetate, magnesium acetate, sodium nitrate, sodium carbonate and manganese acetate. Particularly advantageous results are achieved with sodium acetate, potassium acetate, lithium hydroxide, iron acetate and manganese acetate.

The said salts are suitably added in amounts of from about 0.001 to 2 percent by weight, especially from 0.01 to 0.5 percent by weight, based on the dienecarboxylic acid. They dissolve in the reaction mixture and make a special separation process superfluous.

The reaction of the dienedicarboxylic acid is carried out by conventional methods. For example, the 3,5-cyclohexadiene-1,2-dicarboxylic acid is heated with the anhydride of the low molecular weight alkanecarboxylic acid, in the presence of the salt, to the reaction temperature, preferably to the reflux temperature.

Examples of suitable anhydrides of low molecular weight alkanecarboxylic acids are those of alkanecarboxylic acids of 2 to 4 carbon atoms, especially acetic anhydride. Usually, the 3,5-cyclohexadiene-1,2-dicarboxylic acid and the anhydride of the low molecular weight alkanecarboxylic acid are employed in a molar ratio of from 1:1 to 1:10, especially from 1:2 to 1:7, and the salt is added in the amount stated abovel. Up to 50% of the anhydride can be replaced by inert organic solvents, e.g. acetic acid. After brief heating, for example for from about 5 to 10 minutes, the maleic anhydride is added, advantageously in a molar ratio of 3,5-cyclohexadiene-1,2-dicarboxylic acid to maleic anhydride of from 1:0.9 to 1:1.5, especially from 1:1.0 to 1:1.3, and the reaction mixture is kept at the reaction temperature for a further 10–20 minutes. After cooling, separating off the solid constituents which have precipitated and washing them with a low molecular weight alcohol, e.g. methanol, or with acetone, acetic acid or water, the BTA formed is dried.

A continuous method can be employed by, for example, heating the 3,5-cyclohexadiene-1,2-dicarboxylic acid with the appropriate amount of the anhydride of the low molecular weight alkanecarboxylic acid, in the presence of the salt, and pumping the solution through a heating zone in a stirred kettle cascade comprising two or three stirred vessels. The heating zone is kept at the reaction temperature. If acetic anhydride is used and the temperature is kept at from 130° to 138° C, residence times of from 5 to 10 minutes suffice. At other temperatures, correspondingly chosen residence times must be employed. The amount of maleic anhydride corresponding to the cyclohexadienedicarboxylic acid is fed, as a liquid, to the first stirred kettle of the cascade. Residence times of from 10 to 60 minutes have proved suitable; the depend on the size of the vessels and on the rate of throughput and rate of stirring in the stirred kettle cascade. Good mixing by intensive stirring, if appropriate with the aid of baffles in the stirred kettles, is advantageous, so that the BTA which has formed and has crystallized out is discharged at a uniform rate. The reaction temperature in the first kettle of the cascade is advantageously kept at from 120° to 140° C, whilst in the last stirred vessel the mixture is already subjected to cooling to room temperature, giving an almost quantitative precipitate of the BTA. The latter is worked up as in the batchwise method of manufacture.

EXAMPLE 1

173.2 g of crude 3,5-cyclohexadiene-1,2-dicarboxylic acid (97 percent pure, so that the stated amount corresponds to 1 mole of 100 percent pure material), manufactured by electrochemical hydrogenation of o-phthalic acid in dilute sulfuric acid containing dioxane, 0.17 g of sodium acetate (0.1%, based on the crude acid)

and 530 g of acetic anhydride (5 moles) are heated at 135° C, under reflux and whilst stirring, in a 1 liter four-neck flask equipped with a stirrer, thermometer, reflux condenser and tube for addition of solids. The mixture is heated up rapidly, in the course of about 15 minutes. After a reaction time of 10 minutes, the reaction mixture is rapidly cooled to from about 100° to 120° C and 107.5 g (1.1 moles) of maleic anhydride are added to the solution. The reaction mixture is then boiled under reflux for 15 minutes, in the course of which the BTA precipitates. After the reaction has ended, the reaction mixture is cooled to about 15° C by means of ice water and the precipitate is filtered off, washed with methanol and dried. On concentrating the filtrate to half its volume, only traces of BTA are obtained. The yield of bicyclooctenedianhydride is 246 g (= 99.2% of theory); melting point: from 354.5° to 355.5° C.

On following the procedure described in Example 1, but using the salts listed in the Table below, instead of sodium acetate, BTA is obtained in the yield shown.

| Example | Additive | % | % Yjeld |
|---------|----------|------|---------|
| 2 | Na carbonate | 0.05 | 98.7 |
| 3 | Na nitrate | 0.1 | 99.0 |
| 4 | Na hydroxide | 0.08 | 98.6 |
| 5 | K acetate | 0.05 | 99.0 |
| 6 | Li hydroxide | 0.1 | 99.1 |
| 7 | Ca acetate | 0.1 | 98.2 |
| 8 | Mg acetate | 0.1 | 97.7 |
| 9 | Fe acetate | 0.02 | 99.0 |
| 10 | Mn acetate | 0.07 | 99.1 |

COMPARATIVE EXAMPLE

If the reaction described in Example 1 is carried out without addition of one of the salts mentioned, the yield is only 68.5%.

What we claim is:

1. In a process for the manufacture of bicyclo[2,2,2]-oct-7-ene-2,3,5,6-tetracarboxylic acid dianhydride by reacting 3,5-cyclohexadiene-1,2-trans-dicarboxylic acid with maleic anhydride in the presence of an anhydride of a low molecular weight alkanecarboxylic acid at from 50° to 150° C, wherein the 3,5-cyclohexadiene-1,2-trans-dicarboxylic acid is heated in the presence of the anhydride of the low molecular weight alkanecarboxylic acid to the reaction temperature and the maleic anhydride is then added, the improvement comprising: carrying out the heating of the 3,5-cyclohexadiene-1,2-trans-dicarboxylic acid and the anhydride of the low molecular weight alkanecarboxylic acid in the presence of from about 0.001 to 2 percent by weight based on the weight of the dicarboxylic acid of a water-soluble salt of an alkali metal, an alkaline earth metal, zinc, manganese or iron, in which salt the anion contains oxygen, and which salt is dissolved in the reaction mixture.

2. A process as set forth in claim 1, wherein an oxide, hydroxide, carbonate, acetate, oxalate or nitrate of an alkali metal, or an acetate of an alkaline earth metal, zinc, manganese or iron, is used as the water-soluble salt.

3. A process as set forth in claim 1 wherein the amount of said salt is from 0.01 to 0.5% by weight based on the weight of the dicarboxylic acid.

4. A process as set forth in claim 1, wherein the 3,5-cyclohexadiene-1,2-dicarboxylic acid and the anhydride of the low molecular weight alkanecarboxylic acid are employed in a molar ratio of from 1:1 to 1:10.

5. A process as set forth in claim 1, wherein the molar ratio of 3,5-cyclohexadiene-1,2-dicarboxylic acid to maleic anhydride is from 1:0.9 to 1:1.5.

6. A process as set forth in claim 1, wherein the anhydride of a low molecular weight alkanecarboxylic acid which is employed is the anhydride of an alkanecarboxylic acid of 2 to 4 carbon atoms.

7. A process as set forth in claim 6, wherein acetic anhydride is used as the anhydride.

* * * * *